(12) United States Patent
Zavala et al.

(10) Patent No.: US 10,584,081 B2
(45) Date of Patent: Mar. 10, 2020

(54) SOLVENT RECYCLE FROM HEAVIES REMOVAL COLUMN

(71) Applicant: UOP LLC, Des Plaines, IL (US)

(72) Inventors: Raul Zavala, Chicago, IL (US); Charles P. Luebke, Mount Prospect, IL (US); Adam J. Kanyuh, Streamwood, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/588,906

(22) Filed: May 8, 2017

(65) Prior Publication Data
US 2017/0342002 A1 Nov. 30, 2017

Related U.S. Application Data

(60) Provisional application No. 62/341,411, filed on May 25, 2016.

(51) Int. Cl.
*C07C 5/333* (2006.01)
*B01D 3/00* (2006.01)
*C07C 2/56* (2006.01)

(52) U.S. Cl.
CPC ............... *C07C 5/333* (2013.01); *B01D 3/00* (2013.01); *C07C 2/56* (2013.01)

(58) Field of Classification Search
CPC .. C07C 5/333; C07C 5/32; C07C 5/00; C07C 5/327
See application file for complete search history.

(56) References Cited

U.S. PATENT DOCUMENTS

| | | | | |
|---|---|---|---|---|
| 5,942,655 | A | * | 8/1999 | Glover ............... C07C 2/66 585/655 |
| 7,737,317 | B1 | | 6/2010 | Schultz et al. |
| 2009/0312591 | A1 | * | 12/2009 | Schubert ............ C07C 5/333 585/654 |
| 2014/0378725 | A1 | * | 12/2014 | Luebke ............ C07C 5/327 585/324 |
| 2016/0168052 | A1 | * | 6/2016 | Schwint ............ C07C 5/333 568/697 |

OTHER PUBLICATIONS

PCT Search Report dated Sep. 21, 2017 for International Application No. PCT/US2017/030335.

* cited by examiner

*Primary Examiner* — Youngsul Jeong
(74) *Attorney, Agent, or Firm* — Paschall & Associates, LLC; James C. Paschall

(57) ABSTRACT

A process is presented for the recovery of solvent used in an alkylation process. The solvent removes heavy hydrocarbons from a C4 stream. The C4 stream is passed to an alkylation unit to generate an alkylate product. A portion of the solvent is carried over with the C4 stream and needs to be recovered to reduce the aromatics content in the C4 stream, to reduce any deleterious effects of the aromatics in downstream processing.

7 Claims, 1 Drawing Sheet

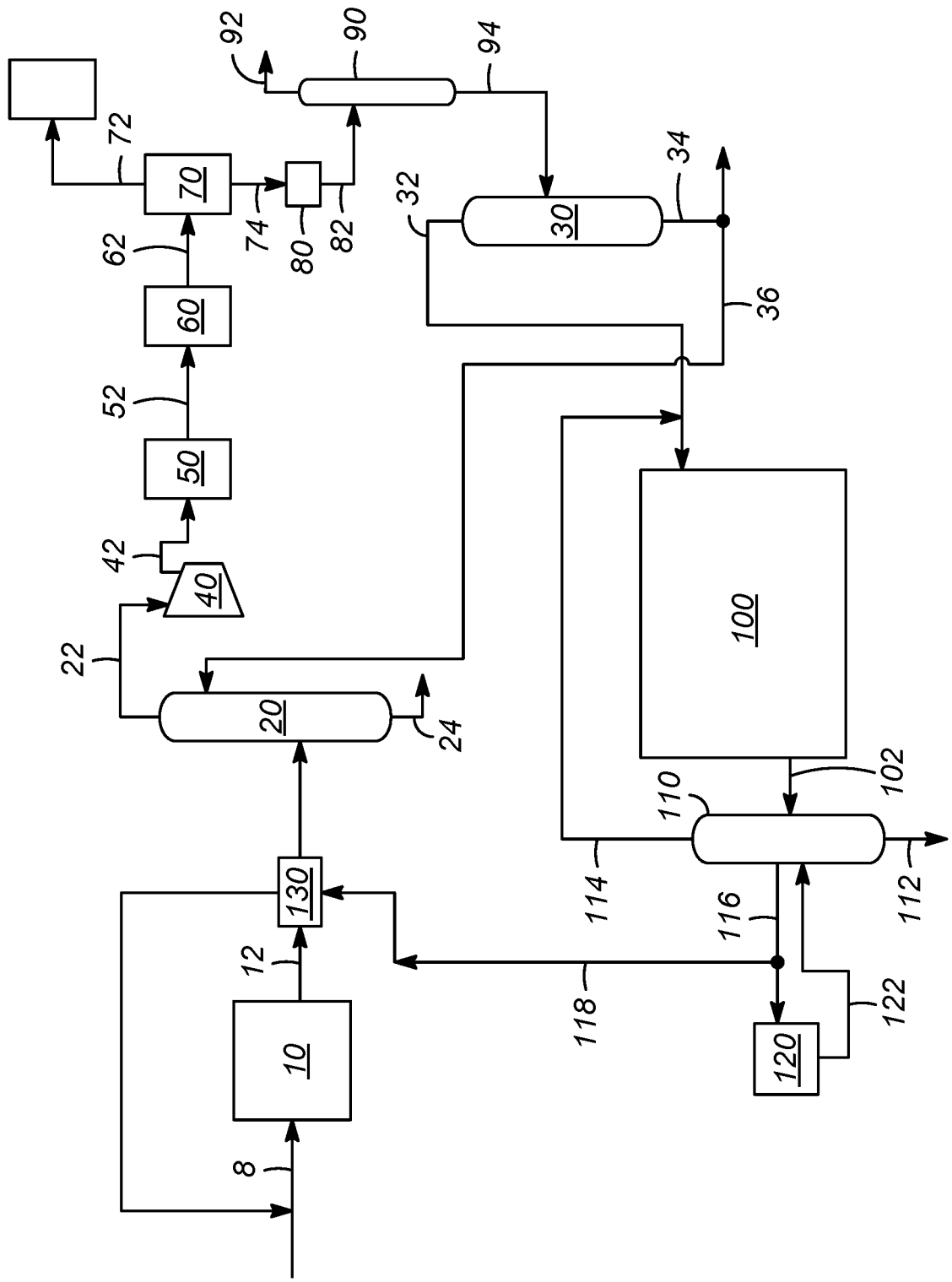

SOLVENT RECYCLE FROM HEAVIES REMOVAL COLUMN

CROSS-REFERENCE TO RELATED APPLICATION

This application claims priority from Provisional Application No. 62/341,411 filed May 25, 2016, the contents of which cited application are hereby incorporated by reference in its entirety.

FIELD OF THE INVENTION

The present invention relates to a radial flow reactor for use in a hydrocarbon conversion process. The process involves the recovery and recycle of solvent in the process of separating olefins from a hydrocarbon stream.

BACKGROUND

A process for the conversion of paraffins to olefins involves passing a normal paraffin stream over a highly selective catalyst, where the normal paraffin is dehydrogenated to the corresponding mono-olefin. The dehydrogenation reaction is achieved under mild operating conditions, thereby minimizing the loss of feedstock.

The typical process involves the use of a radial flow reactor where a paraffin feedstock is contacted with a dehydrogenation catalyst under reaction conditions. The typical process involves dehydrogenating linear paraffins in the C2 to C11 range to produce olefins used as monomers used in the formation of polymers, or as plasticizers, or for dehydrogenating paraffins in the C10 to C14 range to produce linear olefins for the production of linear alkyl benzenes (LABs), and for dehydrogenating paraffins in the C12 to C17 range to produce detergent alcohols or olefin sulfonates.

The process is affected by reactor design, and downstream processing and recovery designs for separation and recovery of the olefins from a hydrocarbon stream. Processing costs can increase substantially if the catalyst is underutilized, if separation components are used up and lost as waste, or if the processing equipment is required to be shut down for maintenance, or operating conditions need to be significantly changed.

SUMMARY

The present invention is a process for producing alkylate, while preserving and recycling solvent used in the process.

A first embodiment of the invention is a process for the recovery of solvent, comprising passing a hydrocarbon stream to a dehydrogenation unit to generate a first process stream comprising olefins; contacting the first process stream with a solvent stream in a contact cooler to generate an olefins stream, and a second process stream comprising solvent; passing the olefins stream to a heavies removal column to generate a heavies overhead stream comprising olefins, and a heavies bottoms stream comprising heavies and recovered solvent; and passing a portion of the heavies bottoms stream to the contact cooler. An embodiment of the invention is one, any or all of prior embodiments in this paragraph up through the first embodiment in this paragraph wherein the portion of the heavies bottoms stream is between 5% and 95% of the bottoms stream. An embodiment of the invention is one, any or all of prior embodiments in this paragraph up through the first embodiment in this paragraph wherein the portion of the heavies bottoms stream is between 25% and 90% of the bottoms stream. An embodiment of the invention is one, any or all of prior embodiments in this paragraph up through the first embodiment in this paragraph wherein the hydrocarbon stream comprises normal butane or isobutane. An embodiment of the invention is one, any or all of prior embodiments in this paragraph up through the first embodiment in this paragraph wherein the contact cooler generates a cooled process stream. An embodiment of the invention is one, any or all of prior embodiments in this paragraph up through the first embodiment in this paragraph wherein the cooled process stream is compressed to generate a compressed stream. An embodiment of the invention is one, any or all of prior embodiments in this paragraph up through the first embodiment in this paragraph wherein the compressed stream is treated in a chloride treater unit to generate a treated stream. An embodiment of the invention is one, any or all of prior embodiments in this paragraph up through the first embodiment in this paragraph wherein the treated stream is passed to separation unit to generate a light stream comprising light gases, and a C4 stream. An embodiment of the invention is one, any or all of prior embodiments in this paragraph up through the first embodiment in this paragraph wherein the effluent stream is passed to a deethanizer or a depropanizer to generate a deethanizer or depropanizer overhead stream and the olefins stream.

A second embodiment of the invention is a process for producing alkylate, comprising passing a butane stream, comprising isobutane to a dehydrogenation unit to generate a first process stream comprising butenes; passing the first process stream and a cooling solvent to a contact cooler to generate a cooled process stream; passing the cooled process stream to a treatment unit to generate a treated stream comprising butenes; passing the treated stream to a heavies removal column to generate an overhead stream comprising butenes, and a bottoms stream comprising heavies and solvent; passing the overhead stream to an alkylation unit to generate an alkylate process stream; and passing a portion of the bottoms stream to the contact cooler, wherein the bottoms stream comprises a part of the cooling solvent. An embodiment of the invention is one, any or all of prior embodiments in this paragraph up through the second embodiment in this paragraph wherein the portion of the bottoms stream is between 25% and 95% of the bottoms stream. An embodiment of the invention is one, any or all of prior embodiments in this paragraph up through the second embodiment in this paragraph further comprising passing the alkylate process stream to a debutanizer to generate an alkylate product stream and a C4 overhead stream. An embodiment of the invention is one, any or all of prior embodiments in this paragraph up through the second embodiment in this paragraph further comprising passing the C4 overhead stream to a deisobutanizer to generate an iso-C4 overhead stream comprising isobutene, and a stream comprising normal C4s; and passing a portion the iso-C4 overhead stream to the alkylation unit. An embodiment of the invention is one, any or all of prior embodiments in this paragraph up through the second embodiment in this paragraph further comprising passing a portion of the iso-C4 overhead stream to the dehydrogenation unit. An embodiment of the invention is one, any or all of prior embodiments in this paragraph up through the second embodiment in this paragraph further comprising passing the stream comprising normal C4s. to the dehydrogenation unit.

A third embodiment of the invention is a process for producing alkylate with reduced solvent consumption, comprising passing a first process stream comprising butenes to a contact cooler; passing a solvent stream to the contact cooler to generate a cooled process stream, and a waste solvent stream; passing the cooled process stream to a C4 recovery unit to generate a light gas stream, a C2-stream, and a C4 process stream; passing the C4 process stream to a heavies removal column to generate a C4 overhead stream comprising C4 olefins, and a bottoms stream comprising solvent and C5+ hydrocarbons; passing the C4 overhead stream to an alkylation unit to generate an alkylate process stream; and passing a portion of the bottoms stream to the contact cooler, wherein the bottoms stream comprises a part of the cooling solvent. An embodiment of the invention is one, any or all of prior embodiments in this paragraph up through the third embodiment in this paragraph wherein the portion of the bottoms stream is between 25% and 95% of the bottoms stream. An embodiment of the invention is one, any or all of prior embodiments in this paragraph up through the third embodiment in this paragraph wherein recovering the C4 process stream from the recovery unit comprises passing the cooled process stream to a compressor to generate a compressed stream; passing the compressed stream to a chloride treater to generate a treated stream; passing the treated stream to a drier to generate a dried stream; passing the dried stream to a cold box separation unit to generate a light gas stream and a condensed C4 stream; and passing the condenses C4 stream to a deethanizer to generate a C2-overhead stream and the C4 process stream. An embodiment of the invention is one, any or all of prior embodiments in this paragraph up through the third embodiment in this paragraph further comprising passing the alkylate process stream to a light ends separation unit to generate a C4 stream, and an alkylate product stream. An embodiment of the invention is one, any or all of prior embodiments in this paragraph up through the third embodiment in this paragraph further comprising passing the C4 stream to a deisobutanizer unit to generate an n-C4 stream and a iso-C4 stream; passing the iso-C4 stream to the alkylation unit.

In the foregoing, all temperatures are set forth in degrees Celsius and, all parts and percentages are by weight, unless otherwise indicated.

Other objects, advantages and applications of the present invention will become apparent to those skilled in the art from the following detailed description and drawings.

BRIEF DESCRIPTION OF THE DRAWING

The FIGURE shows the process of recovering and recycling solvent used to remove the heavies in a C4 process stream.

DETAILED DESCRIPTION

Butenes and butadienes are important chemical precursors for rubbers, polymers, and other materials used in common products. Isobutylene is also used in the production of alkylate, wherein the alkylate which can be used in a blending pool for gasoline.

The alkylation of C4 olefins to form alkylate is performed in a sulfuric acid alkylation process. The process of alkylation of the C4 olefins requires the removal of heavy hydrocarbons, including C5+ hydrocarbons and aromatics that can be generated in the dehydrogenation process reactors. The C4 olefins also needs to minimize any coke build-up from other reactor and downstream equipment, such as the compressors and coolers. The process for purifying the C4 olefin stream includes contacting the process stream with a highly aromatic solvent. The alkylation unit has a design requirement of a maximum aromatic content of 100 wt. ppm, and the aromatic solvent is removed with a heavies removal fractionation unit. The solvent is expensive, and it has been found that a substantial amount of the solvent can be recycled with a drag stream sent to storage. This reduces the need to add replacement solvent in the process.

The present invention, as shown in the FIGURE, passing a hydrocarbon stream 8 to a dehydrogenation unit 10 to generate a first process stream 12 comprising olefins. The first process stream 12 is passed to a contact cooler 20. A solvent stream is passed to the contact cooler 20 to generate a cooled olefins stream 22, and a second process stream 24 comprising solvent and heavy hydrocarbons. The contact cooler 20 provides for removal of heavy hydrocarbons generated in the dehydrogenation unit 10. The olefins stream 22 is passed to a heavies removal column 30 to generate a heavies overhead stream 32 and a heavies bottom stream 34 comprising solvent. A portion 36 of the heavies bottoms stream is passed to the contact cooler 20. The process is directed to the production of alkylate, and in a preferred embodiment, the hydrocarbon stream 8 is a butane stream. The butane stream 8 can comprise normal butane, or isobutane or a mixture thereof.

The portion 36 is between 5% and 95% of the heavies bottoms stream 34. In another embodiment, the portion 36 is between 25% and 90% of the heavies bottom stream 34.

In one embodiment, the cooled process stream 22 is passed to a compressor 40 to generate a compressed stream 42. The compressed stream 42 is passed to a chloride treater unit 50 to generate a treated stream 52. The treated stream 52 is passed to a drying unit 60 to remove residual moisture and to generate a dried stream 62. The dried stream 62 is passed to a separation unit 70 to generate a light stream 72, comprising light gases, and a C4 stream 74. The light gases comprise H2, light hydrocarbons, such as C1 to C3 hydrocarbons, and other non-condensable gases, such as nitrogen (N2) and carbon dioxide (CO2).

The C4 stream can comprise C5+ hydrocarbons, and some dissolved light hydrocarbons. The C4 stream can be passed to a selective hydrogenation unit 80 to hydrogenation acetylenes and diolefins, and to generate a C4 stream with reduced acetylenes and diolefins 82. The reduced C4 stream 82 is passed to a deethanizer 90 to remove any residual light hydrocarbons and gases and generates a light gas overhead stream 92 and a C4 bottoms stream 94. The C4 bottoms stream includes solvent that has been carried over from the contact cooler 20, and is passed to the heavies removal column 30. This column 30 recovers the solvent and recycles a portion 36 back to the contact cooler 20.

The portion 36 is between 25% and 95% of the bottoms stream 34. The heavies overhead stream 32 is passed to an alkylation unit 100 and generates an alkylate process stream 102 comprising alkylate and unreacted C4 compounds.

In one embodiment, the process can include passing the alkylate process stream 102 to a debutanizer 110 to generate an alkylate product stream 112 and a C4 overhead stream 114. The C4 stream 114 can be passed back to the alkylation unit 100. In another embodiment, the debutanizer 110 is a deisobutanizer. The deisobutanizer is a column that includes a side draw 116. The overhead 114 of the deisobutanizer column 110 comprises isobutane. The deisobutanizer can be a divided wall column, or can be a normal column with a side draw. The side draw 116 comprises normal butane, and can be passed to an isomerization unit 120 to generate an isomerized stream 122. The isomerized stream 122 comprised isobutane and n-butane, and is passed back to the deisobutanizer column 110.

A portion 118 of the side draw 116 can be passed to the dehydrogenation unit 10 to generate more butenes. The portion 118 can be passed to a combined feed heat exchanger 130 to preheat the portion 118. Additionally, the portion 118 can first passed to the separation unit 70 to heat exchange with the dried C4 stream in the separation unit 70 to preheat the portion 118, before passing the combined feed heat exchanger 130.

In one embodiment, a portion of the isobutane stream from the deisobutanizer can be passed to the dehydrogenation unit 10 to generate more isobutylene.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for recovery of solvent, comprising:
   passing a hydrocarbon stream to a dehydrogenation unit to generate a first process stream comprising olefins;
   contacting the first process stream with a solvent stream in a contact cooler to generate an olefins stream, and a second process stream comprising solvent;
   passing the olefins stream to a cold box separation unit to separate a light gases stream from a condensed stream, wherein the light gases stream from the cold box separation unit comprises hydrogen, C1 to C3 hydrocarbons, non-condensable gases, or any combination thereof;
   passing the condensed stream to a selective hydrogenation unit to generate a condensed stream having reduced acetylenes;
   passing the condensed stream having reduced acetylenes to a deethanizer or a depropanizer to generate an overhead stream and a C4 bottoms stream;
   passing the C4 bottoms stream to a heavies removal column to generate a heavies overhead stream comprising olefins, and a heavies bottoms stream comprising C5 + hydrocarbons and solvent; and
   passing a portion of the heavies bottoms stream to the contact cooler.

2. The process of claim 1 wherein the portion of the heavies bottoms stream passed to the contact cooler is between 5 wt.-% and 95 wt.-% of the heavies bottoms stream.

3. The process of claim 2 wherein the portion of the heavies bottoms stream passed to the contact cooler is between 25 wt.-% and 90 wt.-% of the heavies bottoms stream.

4. The process of claim 1 wherein the hydrocarbon stream comprises normal butane or isobutane or a mixture of normal butane and isobutane.

5. The process of claim 1 wherein the olefins stream is compressed to generate a compressed stream.

6. The process of claim 5 wherein the compressed stream is treated in a chloride treater unit to generate a treated stream.

7. The process of claim 6 wherein the treated stream is passed to the cold box separation unit.

* * * * *